United States Patent [19]

Okazaki et al.

[11] Patent Number: 5,286,872
[45] Date of Patent: Feb. 15, 1994

[54] DEUTERATED PYRAZOLE COMPOUND

[75] Inventors: Masaki Okazaki; Nobuharu Nozaki; Nobuhiko Uchino, all of Kanagawa, Japan

[73] Assignee: Fuji Film Co., Ltd., Kanagawa, Japan

[21] Appl. No.: 879,350

[22] Filed: May 7, 1992

[30] Foreign Application Priority Data

May 21, 1991 [JP] Japan .................. 3-144201

[51] Int. Cl.⁵ .......................... C07D 231/12
[52] U.S. Cl. .............................. 548/377.1
[58] Field of Search ............... 548/373, 377.1

[56] References Cited

FOREIGN PATENT DOCUMENTS 210432 6/1987 Japan .

Primary Examiner—Robert W. Ramsuer
Attorney, Agent, or Firm—Sughrue, Mion, Zinn, Macpeak & Seas

[57] ABSTRACT

3,5-Dimethyl-1-(4-nitrophenyl) pyrazole having at least one deuterium atom and a non-linear optical material comprising the same is described herein.

3 Claims, 5 Drawing Sheets

DEUTERATED PYRAZOLE COMPOUND

FIELD OF THE INVENTION

This invention relates to a deuterium substitution product of a compound and its use as a non-linear optical material.

BACKGROUND OF THE INVENTION

In recent years, materials which are non-linear between a polarization and an electric field, said fields appearing after exposure to a strong optical field such as a laser light, have attracted attention.

Such materials are generally known as non-linear optical materials, and are described in detail in the following publications: "Nonlinear Optical Properties of Organic and Polymeric Material", ACS SYMPOSIUM SERIES 233, edited by David J. Williams (American Chemical Society, 1983); "Organic Nonlinear Optical Materials", under the supervision of Masao Kato and Hachiro Nakanishi (C.M.C. Company, 1985); and "Nonlinear Optical Properties of Organic Molecules and Crystals", Vols. 1 and 2, edited by D. S. Chemla and J. Zyss, (Academic Press Company, 1987).

One utility of the non-linear optical material is as a wavelength conversion device, useful in the development of a second harmonic generation (SHG) which is based on a secondary non-linear effect and an addition of frequencies and a subtraction of frequencies. What has been used actually heretofore is an inorganic perovskite typified by lithium niobate. In recent years, it has been found that a $\pi$-electron conjugated-type organic compound, having an electron donative group and an electron attractive group, has various properties as a non-linear optical material, which greatly upgrades the above-mentioned inorganic material.

For the formation of a secondary non-linear optical material having higher properties, compounds having high non-linear sensitivity in a molecular state should be aligned so as not to generate inverse symmetry. It is known that for the generation of high non-linear sensitivity, compounds having a long $\pi$-electron conjugated chain are useful. As described in the above-mentioned publications, it is evident that in these $\pi$-electron conjugated compounds, the absorption maximum wavelength increases, and the transmittance of blue light decreases. This result is detrimental with respect to generation of blue light as a second harmonic. This also occurs when using a p-nitroaniline derivative. For generating a second harmonic, the effect of the transmittance of the p-nitroaniline derivative's wavelength is great as is shown in Plain Azema, et al., Proceedings of SPIE, Vol. 400, New Optical Materials, (1983), page 186, FIG. 4.

Accordingly, a non-linear optical material having a high transmittance to a blue light is desired. Heretofore, investigations have been made to substitute a carbon atom with a nitrogen atom in a benzene ring of nitroaniline, but no satisfactory result has been obtained.

Further improvement has been attempted and many materials are shown in JP-A-62-59934, JP-A-63-23136, JP-A-63-26038, JP-B-63-31768. JP-A-63-163827, JP-A-63-146025, JP-A-63-85526, JP-A-63-239427, JP-A-1-100521, JP-A-64-56425, JP-A-1-102529, JP-A-1-102530, JP-A-1-237625 and JP-A-1-207724. (The term "JP-A" means unexamined published Japanese patent application and "JP-B" means examined Japanese patent publication.)

The present inventors have disclosed an excellent method in JP-A-62-210430 and JP-A-62-210432.

Particularly, 3,5-dimethyl-1-(4-nitrophenyl) pyrazole, disclosed in JP-A-62-210432, provides for a non-linear optical constant of maximum value, which comprises a tensor component of an off diagonal element capable of phase matching among heretofore known organic non-linear optical materials, and is a very useful compound.

In addition to the transmission of the second harmonic to be generated as mentioned above, attention should be paid to the transmission of the fundamental wave to be contained in the non-linear optical material. This has been widely studied in the investigations of plastic optical fibers. It has been made clear that in the case of organic high molecular materials, an absorption is seen in the vicinity of 1 $\mu$m, and results in propagation loss. It is considered that this absorption in the vicinity of 1 $\mu$m is due to the triplicate wave of stretching vibration of a carbon-hydrogen bond, a nitrogen-hydrogen bond, or an oxygen-hydrogen bond. By replacing the hydrogen atom of these bonds with a deuterium atom, the absorption strength can be curtailed, as described in JP A-54-65556, JP-A-57-81204, JP-A-57-142601, JP-A-58-149003, JP-A-58-154803, JP-A-61-20906, and JP-A-61-223805.

In the field of organic non-linear optical materials, a description of deuterium compounds is seen in JP-A-49-81051, JP-A-63-21627, JP-A-63-163825, JP-A-2-149825, and JP-A-2-247620. DLAP (Deutrated L-Arginine Phosphate) obtained by partly deuteration of LAP is well-known. However, these described compounds do not have sufficient properties, and deuterated compounds derived from compounds having excellent properties are desired.

SUMMARY OF THE INVENTION

It is an object of this invention, therefore, to provide a deuterated compound of a compound having excellent properties as a non-linear optical material.

As a result of extensive investigations, the present inventors have found that the object of this invention can be achieved by 3,5-dimethyl-1-(4-nitrophenyl) pyrazole having at least one deuterium atom.

The number of deuterium atoms is preferably at least 4. Particularly, the pyrazole ring portion is entirely occupied by deuterium atoms.

DETAILED DESCRIPTION OF THE INVENTION

Figure 1:
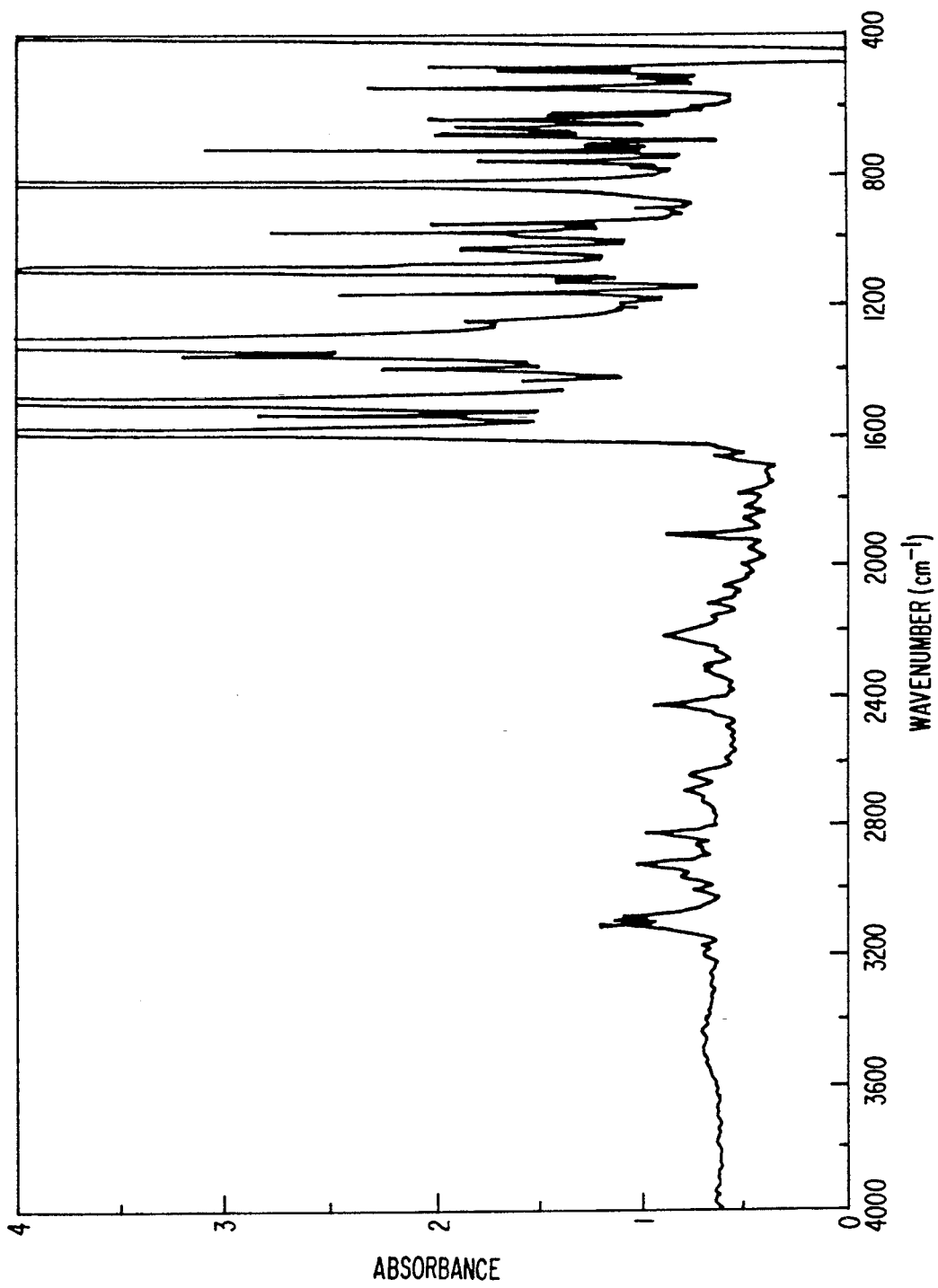
FIG. 1 is an infrared absorption spectrum of Compound 1.

Specific examples of the compound of the present invention will be shown below.

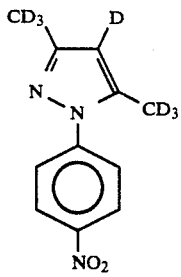

1.

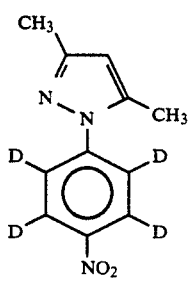

2.

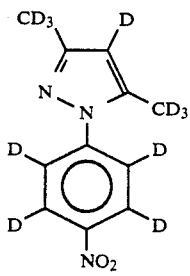

3.

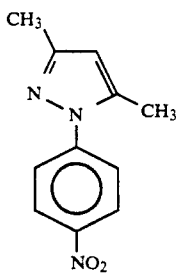

DMNP

These compounds may be synthesized by using an aromatic nucleophilic substitution reaction of a 3,5-dimethylpyrazole derivative to a 4-halogenonitrobenzene derivative or by a ring-closing reaction to pyrazole with a 4-nitrophenylhydrazine derivative or a 4-nitrobenzenediazonium salt derivative and an acetylacetone derivative.

When an aromatic nucleophilic substitution reaction is used, generally heating is carried out by using a solvent in the presence of a basic catalyst. Examples of a basic catalyst include inorganic bases such as alkali metals or alkaline earth metals and organic bases such as amines. Of these, inorganic bases are preferred, and among them, carbonates of alkali metals such as sodium carbonate, sodium hydrogen carbonate and potassium carbonate are preferred. The solvent may be selected from polar solvents such as N,N-dimethylformamide (DMF) and dimethyl sulfoxide (DMSO) and non-polar solvents such as benzene and hexane. Of these, aprotic solvents are preferred. Among them, polar solvents such as DMF and DMSO are preferred. The reaction temperature may be 25° to 180° C., preferably 40° to 150° C., especially preferably 60° to 130° C.

A ring-closing reaction using a hydrazine derivative and a diazonium salt derivative can also be used to prepare the compounds of the present invention. Details of this reaction can be found in the description of R. C. Elderfield edited, "Heterocyclic Compounds", Vol. 5, Chapter II, pages 45 to 161, John Wiley & Sons, New York, 1957 may be referred to.

The ring-closing reaction may be preferably carried out in the presence of an acid or a basic catalyst, more preferably using an acid. Especially preferred are inorganic acids such as hydrochloric acid and sulfuric acid. The solvent may be selected from polar solvents such as water, DMF, and DMSO, and non-polar solvents such as benzene and hexane. Among these, protic solvents such as water and alcohols are preferred. Water is especially preferred. The reaction temperature can be 20° to 200° C., preferably 50° to 160° C., especially preferably 80° to 140° C.

The invention will be illustrated by the following non-limiting Examples.

EXAMPLE 1

Synthesis of Compound 1

1) Synthesis of Acetylacetone ($d_7$)

It was synthesized by the description of Journal of the American Chemical Society, Vol. 99, page 4572 (1977), or ibid., Vol. 75, page 5030 (1953).

2) Synthesis of Compound 1

80 ml of 12% deuterium chloride aqueous solution was added to 5.72 g (53 millimoles) of acetylacetone ($d_7$) and 7.96 g (52 millimoles) of 4-nitrophenylhydrazine. The mixture was stirred at 60° C. for 4 hours. Three g of active carbon was added while the mixture was hot. The mixture was then stirred for about 5 minutes. The resulting mixture was suction-filtered, thereby removing the active carbon and the insoluble matter. The resulting filtrate was cooled with ice, and a solution composed of 14 g of sodium hydroxide and 53 ml of deuterium oxide was gradually added. The collected crystals were taken by filtration and washed with deuterium oxide. After air-drying, the mixture was recrystallized two times with isopropanol using active carbon to obtain 2.6 g (Yield 22.3%) of the desired compound. The melting point of the compound was 102°-103° C.

The deuterated ratio was examined by $^1$H—Nuclear Magnetic Resonance Spectroscopy. The methyl groups of the 3-position and 5-position were both 90% deuterium, and the hydrogen at the 4-position was 95% deuterium.

Figure 2:
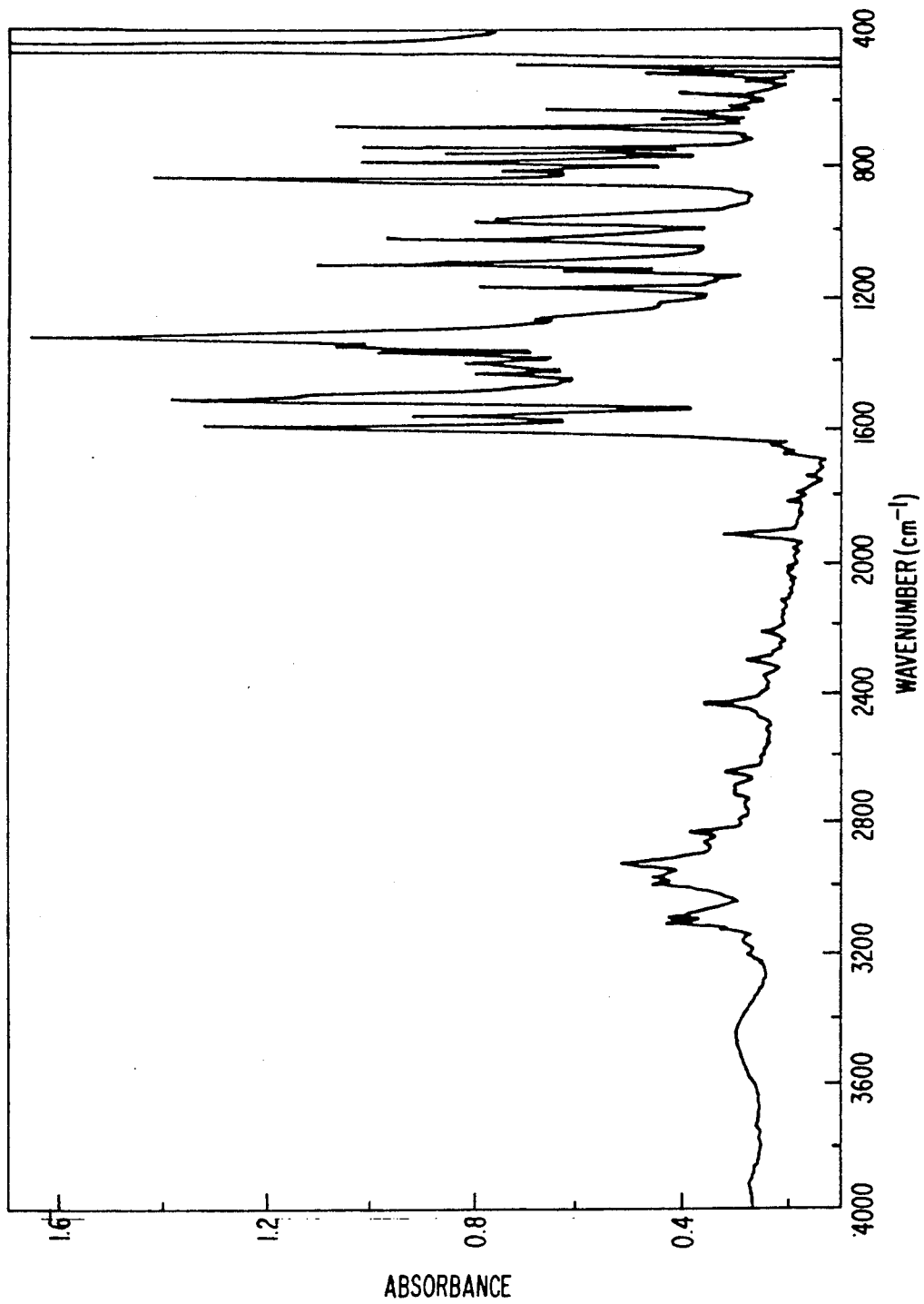
FIG. 2 is an infrared absorption spectrum of DMNP.

FIGS. 1 and 2 show infrared spectra of compound 1 and a compound not deuterated (DMNP). It was seen that the absorption strength of $v_{C-H}$ decreased.

Compounds 2 and 3 can be Synthesized in accordance with Scheme 1.

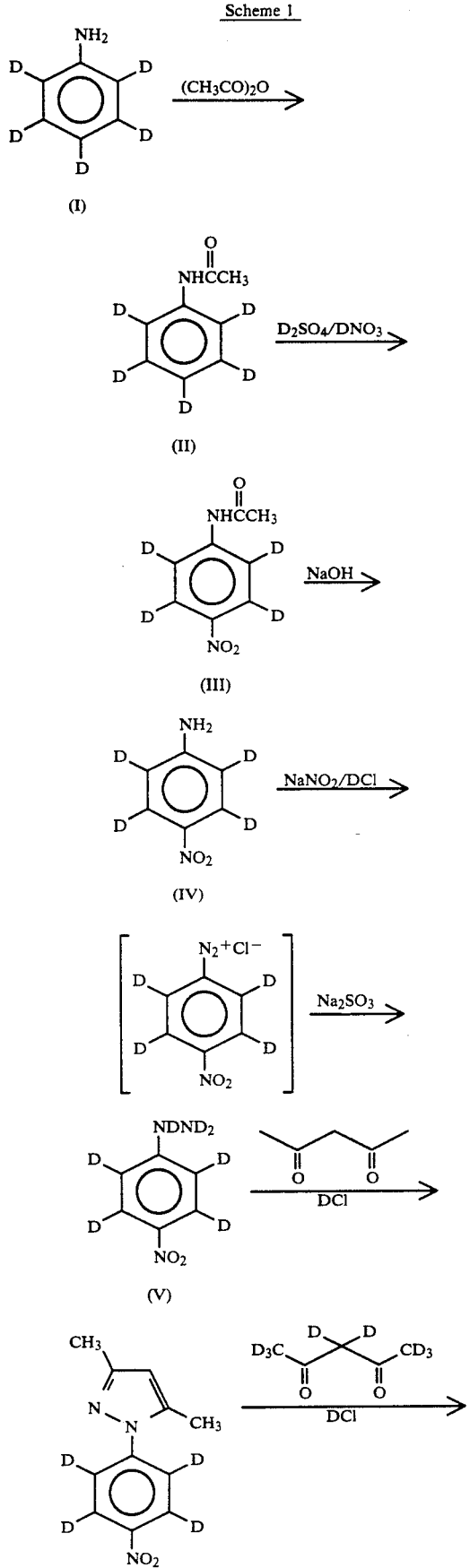

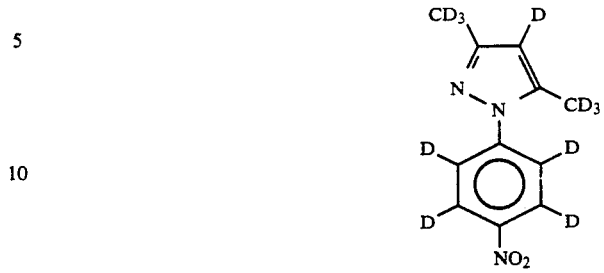

EXAMPLE 2

Synthesis of Compound 2

1) Synthesis of Compound (II)

While stirring, 52 g of acetic anhydride (0.51 mole) was added to a solution of 50 g (0.51 mole) of Compound (I) in 100 ml of anhydrous benzene thereby allowing the solvent to slowly boil. After the addition, the solution was cooled to room temperature. The precipitated crystals were collected by filtration, washed with n-hexane and reduced under pressure and dried to obtain Compound (II). The amount yielded was 64 g (yield 90%).

2) Synthesis of Compound (III)

A mixture of 150 ml of a 68% deuterium oxide solution of deuterated nitric acid and 150 ml of a 98% deuterium oxide solution of deutrated sulfuric acid was cooled to 10° C. with an ice bath. While stirring, 64 g (0.46 mole) of Compound (II) was slowly added so that the reaction mixture did not exceed 20° C. After addition, the mixture was stirred at room temperature for 1 hour. After the reaction, the reaction mixture was then poured on 650 g of ice, and the resulting precipitated solid was collected by filtration. This precipitate was recrystallized with ethanol to give Compound (III). The amount yielded was 46 g (yield 54%).

3) Synthesis of Compound (IV)

An amount of 46 g (0.25 mole) of Compound (III) was added little by little to a solution composed of 23 g (0.58 mole) of sodium hydroxide, 40 ml of water and 250 ml of ethanol. The resulting mixture was then heated under reflux for 1 hour. After the reaction, 300 ml of water was added dropwise with stirring to precipitate the desired compound. The resulting compound was cooled with an ice bath, collected by filtration, and recrystallized from ethanol to obtain Compound (IV). The amount yielded was 33 g (yield 92%).

4) Synthesis of Compound (V)

Compound (IV) in an amount of 33 g (0.23 mole) was dissolved in 65 ml of 37% of deuterium chloride aqueous solution, and with ice cooling, the inside temperature was maintained to 0° to 5° C. A solution of 19.2 (0.28 mole) of sodium nitrite in 32 ml of deuterium oxide was added dropwise with stirring to cause diazotization. Then, 67 g (0.53 mole) of sodium nitrite and 12.8 g (0.32 mole) of sodium deuteroxide were dissolved in 320 ml of deuterium oxide. Under ice cooling to maintain the inside temperature at 0° to 5° C., the resulting diazonium salt solution was added dropwise while stirring.

After dropwise addition, 300 ml of a 37% deuterium chloride aqueous solution was added. The reaction mixture was heated to an inside temperature of 55° C., and 64 ml of 37% deuterium chloride aqueous solution was added. While maintaining the inside temperature at 70° to 80° C., the mixture was heated with stirring for 10 minutes. The reaction mixture was filtered, and neutralized with sodium carbonate to precipitate the desired product. After collection by filtration, recrystallization from ethanol was performed to obtain Compound (V). The amount yielded was 24 g (yield 72%).

5) Synthesis of Compound 2

An 80 ml amount of 12% of deuterium chloride aqueous solution was added to 5.3 g (53 millimoles) of acetylacetone and 7.6 g (52 millimoles) of Compound (V). The mixture was stirred at 60° C. for 4 hours. While hot, 3 g of active carbon was added, and the mixture was stirred for about 5 minutes. The resulting mixture was suction-filtered to eliminate the active carbon and insoluble matter. The filtrate was then cooled with ice, and a solution composed of 14 g of sodium hydroxide and 53 ml of deuterium oxide was slowly added. The collected crystals were taken by filtration and washed with deuterium oxide. After air drying, the mixture was recrystallized twice with isopropanol using active carbon to obtain Compound 2. The amount yielded was 2.9 g (yield 25.0%). The melting point was determined to be 102°–103° C.

Figure 3:
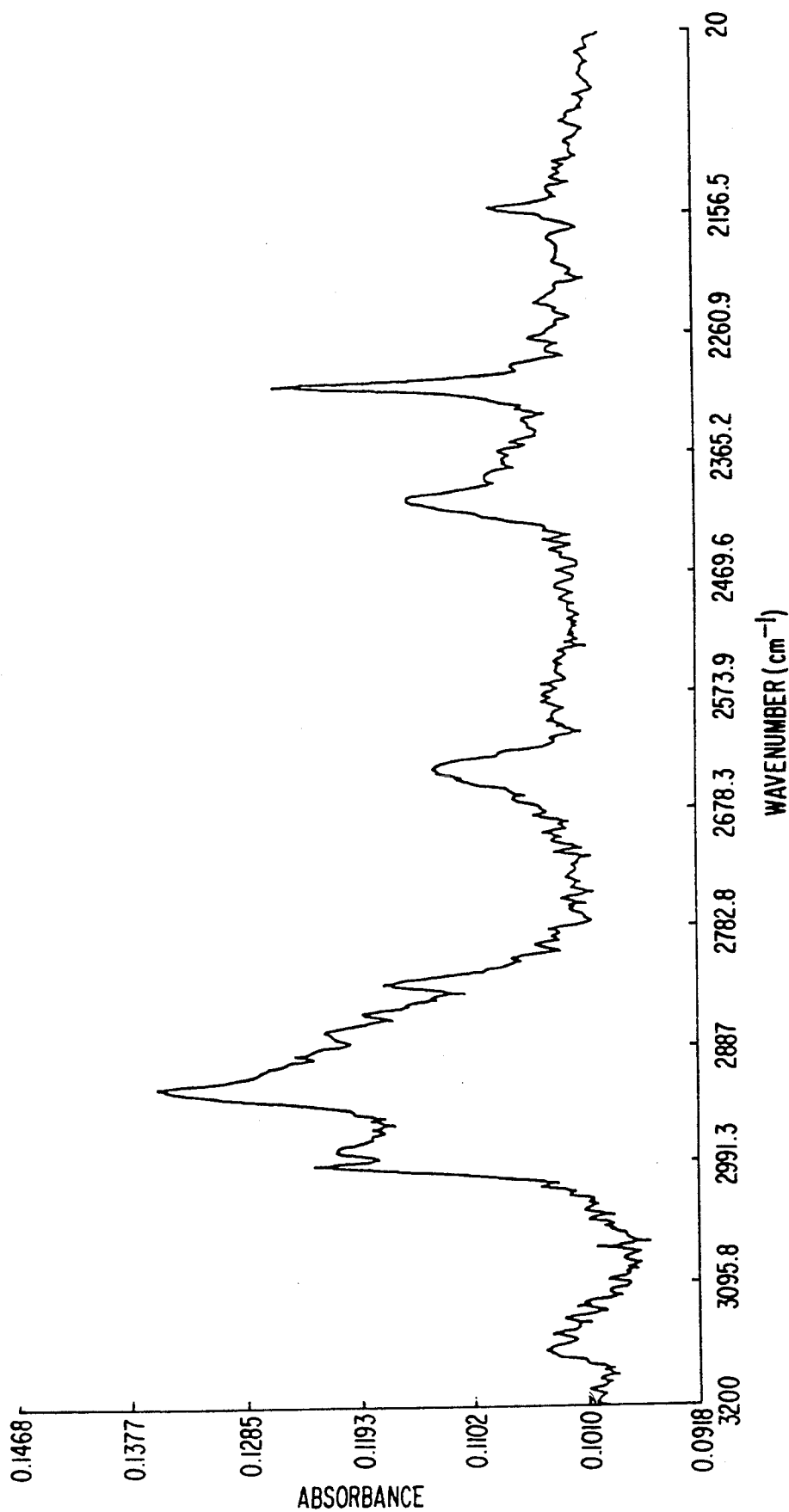
FIG. 3 is an infrared absorption spectrum of Compound 2.

FIG. 3 shows an infrared absorption spectrum of Compound 2. As compared to FIG. 2, it is apparent that the absorption of $v_{C-H}$ is decreased.

EXAMPLE 3

Synthesis of Compound 3

An 80 ml amount of 12% deuterium chloride aqueous solution was added to 5.72 g (53 millimoles) of acetylacetone (d$_7$) and 7.6 g (52 millimoles) of Compound (V). The mixture was stirred at 60° C. for 4 hours. While the solution was still hot, 3 g of active carbon was added. The resulting mixture was stirred for about 5 minutes and then suction-filtered to eliminate the active carbon and insoluble matter. The filtrate was cooled with ice, and a solution consisting of 14 g of sodium hydroxide and 53 ml of deuterium oxide was gradually added. The resulting precipitated crystals were taken up by filtration and washed with deuterium oxide. After air-drying, the mixture was recrystallized twice with isopropanol using the active carbon, thereby obtaining Compound 3. The amount yielded was 2.8 g (yield 23.2%). The melting point was determined to be 102°–103° C.

Figure 4:
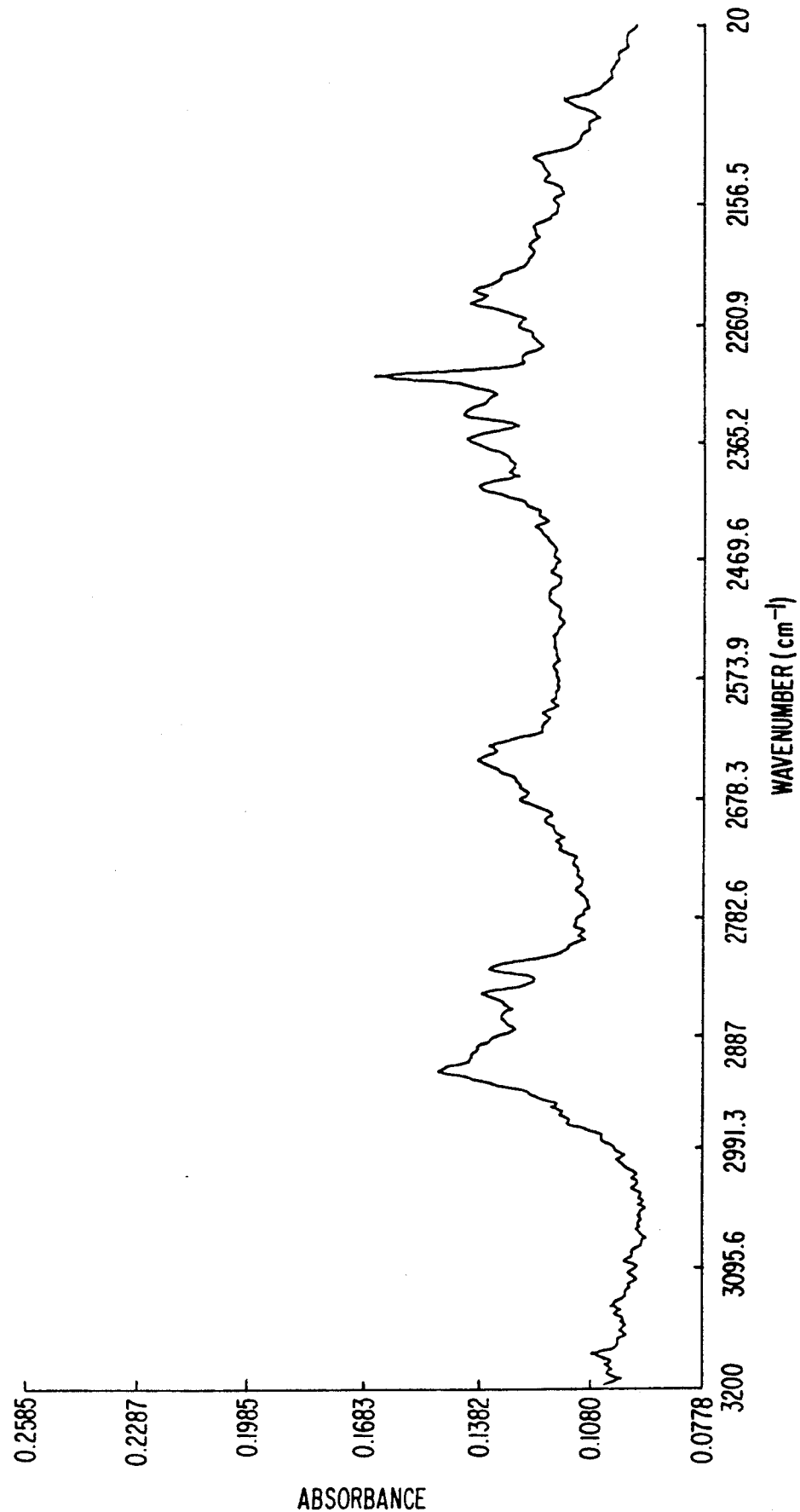
FIG. 4 is an infrared absorption spectrum of Compound 3.

FIG. 4 shows an infrared absorption spectrum of Compound 3. As compared to FIG. 2, it is apparent that the absorption of $v_{C-H}$ is decreased.

EXAMPLE 4

The measurement of the second harmonic generation was made on a fine crystalline powder of a compound of this invention by the method described in S. K. Kurtz, and R. T. Perry, Journal of Applied Physics, Vol. 39, page 3798 (1968).

Figure 5:
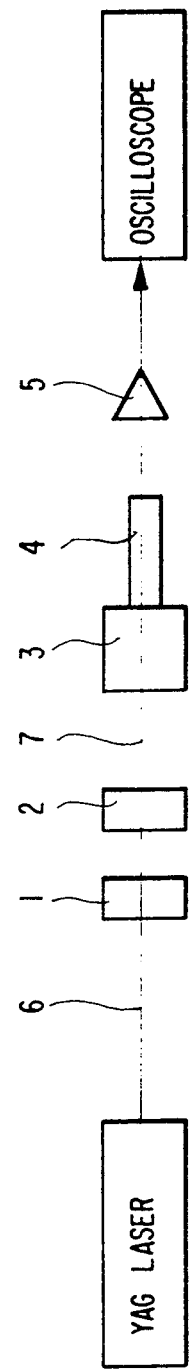
FIG. 5 shows an SHG strength measuring apparatus using a powder.

The measurement was made by using the apparatus shown in FIG. 5.

In FIG. 5, (1) represents a powdery sample, (2) represents a basic wave cut filter, (3) represents a spectrograph, (4) represents a photo-multiplier, (5) represents an amplifier, (6) represents a light having a wavelength of 1.064 μm (fundamental wave), and (7) represents a light having a wavelength of 0.532 μm (second harmonics).

The strength of the second harmonic was measured by the evaluating apparatus shown in FIG. 5 by using a pulse YAG laser light ($\lambda = 1.064$ μm, beam diameter$\doteq$1 mm $\theta$, peak power$\doteq$10 Mw/cm$^2$) as a fundamental wave. The measurement was made by making a comparison with the strength of the second harmonic of urea. When the strength was weak, observation was made by using a visual observation. To distinguish emission by two photon wavelength absorptions of a fundamental wave (mainly emission of yellow and red) from the second harmonic, a spectrograph was put in so that only the second harmonic would be measured.

As a result, Compounds 1, 2 and 3 generated about 16 times second harmonics as in the case of urea. Hence, the compounds of this invention are useful as non-linear optical materials.

A single crystal of Compound 1 was subjected to X-ray crystal structure analysis, and it showed the same space group Pca2$_1$ as DMNP and it showed the almost same lattice constant as DMNP as Table 1 below. This means that Compound 1 has the same crystalline structure as DMNP, and therefore, has the same non-linear optical characteristics as DMNP.

TABLE 1

| | Space Group | Lattice Constant a | b | c |
|---|---|---|---|---|
| Compound 1 | Pca2$_1$ | 21.386Å | 3.964Å | 12.587Å |
| DMNP | Pca2$_1$ | 21.383Å | 3.961Å | 12.604Å |

DMNP, as described in Proceedings of International Workshop on Crystal Growth of Organic Materials, P256 (1989, 12. 7–9), is an excellent non-linear material. The deuterated compounds of this invention having the same non-linear optical properties as DMNP are, therefore, very useful as non-linear optical materials.

EXAMPLE 5

A single crystal of Compound 1 and DMNP for comparison was prepared according to the Bridgeman-Stockberger method. Each of the single crystal was irradiated with a Nd-YAG laser of 1064 nm. Then, the temperature elevation of these crystals was evaluated using a thermo-camera. As a result, when 1W was input, the temperature elevation of Compound 1 was 0.7° C., while that of DMNP was 3.0° C.

This result reveals that the temperature elevation due to light absorption can be reduced by deuteration.

When the temperature is elevated, it occurs an adverse influence such as sublimation and decomposition. Such adverse influences can be prevented by deuteration and a stable wavelength converting wave can be obtained.

The purposes of this invention is to provide a non-linear optical material having excellent non-linear optical properties, which curtails the absorption strength and limits the stretching vibration by changing a carbon-hydrogen bond to a carbon-deuterium bond.

While the invention has been described in detail and with reference to specific embodiments thereof, it will be apparent to one skilled in the art that various changes and modifications can be made therein without departing from the spirit and scope thereof.

What is claimed is:

1. A 3,5-Dimethyl-1-(4-nitrophenyl) pyrazole selected from the group consisting of Compound 1 and Compound 3:
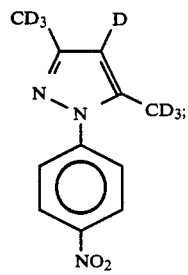
1.
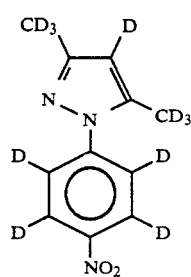
3.
2. The pyrazole compound of claim 1, wherein said compound is:
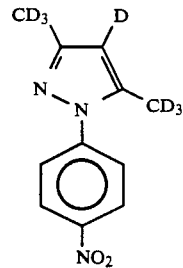
1.
3. The pyrazole compound of claim 1 wherein said compound is:
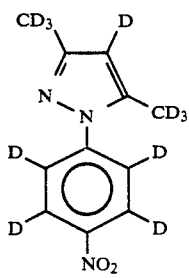
3.
* * * * *